United States Patent
Alexander et al.

(10) Patent No.: US 9,259,572 B2
(45) Date of Patent: *Feb. 16, 2016

(54) LEAD OR LEAD EXTENSION HAVING A CONDUCTIVE BODY AND CONDUCTIVE BODY CONTACT

(71) Applicant: Medtronic, Inc., Minneapolis, MN (US)

(72) Inventors: James A. Alexander, Shorewood, MN (US); Michael E. Metzler, Minneapolis, MN (US); Jay K. Lahti, Blaine, MN (US); Robert L. Olson, Vadnais Heights, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/294,067

(22) Filed: Jun. 2, 2014

(65) Prior Publication Data

US 2014/0288626 A1 Sep. 25, 2014

Related U.S. Application Data

(63) Continuation of application No. 14/108,757, filed on Dec. 17, 2013, now Pat. No. 8,744,598, which is a continuation of application No. 13/932,878, filed on Jul. 1, 2013, now Pat. No. 8,620,455, which is a continuation of application No. 11/739,787, filed on Apr. 25, 2007, now Pat. No. 8,483,842.

(51) Int. Cl.
*A61N 1/05* (2006.01)
*A61N 1/08* (2006.01)
*A61N 1/04* (2006.01)

(52) U.S. Cl.
CPC .. *A61N 1/08* (2013.01); *A61N 1/05* (2013.01); *A61N 1/0553* (2013.01); *A61N 1/048* (2013.01); *A61N 1/0488* (2013.01); *A61N 2001/086* (2013.01)

(58) Field of Classification Search
CPC ....... A61N 1/048; A61N 1/0488; A61N 1/05; A61N 1/08; A61N 2001/086
USPC .................................. 607/115–117, 119, 122
See application file for complete search history.

(56) References Cited

U.S. PATENT DOCUMENTS 2,433,480 A 12/1947 Rendich
2,487,038 A 11/1949 Jasper
(Continued)

FOREIGN PATENT DOCUMENTS

EP 0617978 5/1994
EP 0624383 11/1994
(Continued)

OTHER PUBLICATIONS

PCT/US2004/042081: Search Report and Written Opinion.
(Continued)

*Primary Examiner* — Allen Porter, Jr.
(74) *Attorney, Agent, or Firm* — Withers & Keys, LLC

(57) ABSTRACT

An implantable medical device that includes a body that includes a proximal end portion configured to be at least partially received by an apparatus, and a distal end portion; a stimulating electrical element at the distal end portion of the body; a stimulating contact at the proximal end portion of the body, wherein the stimulating contact is positioned such that, when received by the apparatus, at least a portion of the apparatus is capable of electrically coupling to the stimulating contact; a stimulating conductor that electrically couples the stimulating electrical element to the stimulating contact; a conductive body, wherein the conductive body is not utilized for application of stimulation; a conductive body contact, wherein the conductive body is electrically connected to the conductive body contact. Systems that include devices are also disclosed.

18 Claims, 9 Drawing Sheets

(56) References Cited

U.S. PATENT DOCUMENTS

| | | |
|---|---|---|
| 3,788,329 A | 1/1974 | Friedman |
| 3,842,485 A | 10/1974 | Bement |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakeley et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 6,004,269 A | 12/1999 | Crowley et al. |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |
| 6,606,521 B2 | 8/2003 | Paspa et al. |
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |
| 6,673,999 B1 | 1/2004 | Wang et al. |
| 6,675,033 B1 | 1/2004 | Lardo et al. |

(56) References Cited

U.S. PATENT DOCUMENTS

| | | |
|---|---|---|
| 6,689,835 B2 | 2/2004 | Amarasekera et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh et al. |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeh |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |

(56) References Cited

U.S. PATENT DOCUMENTS

| | | |
|---|---|---|
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183438 A1 | 12/2002 | Amarasekera et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1* | 10/2005 | Hoegh et al. ............... 607/116 |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1 | 2/2012 | Olsen |
| 2012/0053664 A1 | 3/2012 | Hegland |
| 2012/0059467 A1 | 3/2012 | Drew |
| 2012/0130461 A1 | 5/2012 | Olsen |
| 2012/0330383 A1 | 12/2012 | Wahlstrand |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |

(56) References Cited

U.S. PATENT DOCUMENTS

| | | |
|---|---|---|
| 2014/0350654 A1 | 11/2014 | Olsen et al. |
| 2015/0082618 A1 | 3/2015 | Hegland |
| 2015/0170792 A1 | 6/2015 | Alford |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| JP | 11-086641 | 3/1999 |
| JP | WO02/00292 | 1/2002 |
| WO | WO95/32673 | 12/1995 |
| WO | WO96/16694 | 6/1996 |
| WO | WO96/28951 | 9/1996 |
| WO | WO97/41923 | 11/1997 |
| WO | WO98/48896 | 11/1998 |
| WO | WO99/10035 | 3/1999 |
| WO | WO99/19020 | 4/1999 |
| WO | WO99/60370 | 11/1999 |
| WO | WO00/27279 | 5/2000 |
| WO | WO01/80940 | 11/2001 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO2004/012809 | 2/2004 |
| WO | WO2004/052448 | 6/2004 |
| WO | WO2004/073040 | 8/2004 |
| WO | WO2005/030322 | 4/2005 |
| WO | WO2005/032654 | 4/2005 |
| WO | WO2005/102444 | 11/2005 |
| WO | WO2005/102445 | 11/2005 |
| WO | WO2005/102446 | 11/2005 |
| WO | WO2005/102447 | 11/2005 |
| WO | WO2006/031317 | 3/2006 |
| WO | WO2006/093685 | 9/2006 |
| WO | WO2006/093686 | 9/2006 |
| WO | WO2006/118640 | 11/2006 |
| WO | WO2006/118641 | 11/2006 |
| WO | WO2007/047966 | 4/2007 |
| WO | WO2007/124273 | 11/2007 |
| WO | WO2007/126657 | 11/2007 |
| WO | WO2007/149757 | 12/2007 |
| WO | WO2008/088568 | 7/2008 |
| WO | WO2008/100839 | 8/2008 |
| WO | WO2008/100840 | 8/2008 |
| WO | WO2008/111986 | 9/2008 |
| WO | WO2008/130409 | 10/2008 |
| WO | WO2008/134196 | 11/2008 |
| WO | WO2008/140376 | 11/2008 |
| WO | WO2009/011440 | 9/2009 |
| WO | WO2009/134901 | 11/2009 |
| WO | WO2010/062988 | 6/2010 |
| WO | WO2010/126871 | 11/2010 |
| WO | WO2010/126877 | 11/2010 |
| WO | WO2010/126884 | 11/2010 |
| WO | WO2010/126887 | 11/2010 |
| WO | WO2010/126935 | 11/2010 |
| WO | WO2010/126939 | 11/2010 |
| WO | WO2010/126943 | 11/2010 |
| WO | WO2010/126946 | 11/2010 |
| WO | WO2010/126949 | 11/2010 |
| WO | WO2010/126975 | 11/2010 |
| WO | WO2010/135440 | 11/2010 |
| WO | WO2011/019416 | 2/2011 |
| WO | WO2012/103419 | 8/2012 |
| WO | WO2013/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0/7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama.net www.cpanorama.net/documents/groundloop/basics.html 28052.00 11/739,787.
Finelli, D., et al., "MRI Imaging-Related Heating of Deep Brain Stimulation Electrodes: In Vitro Study", AJNR Am. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_ati3776/is 200403/ai_n9405_582/print.
Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.
Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.
Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.
Medtronic Activa Product Family and Procedure Solution Brochure, Medtronic, Inc, 2001.
Medtronic Neurostimulation Systems Brochure, Medtronic, Inc., 2002.

(56) References Cited

OTHER PUBLICATIONS

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

* cited by examiner

LEAD OR LEAD EXTENSION HAVING A CONDUCTIVE BODY AND CONDUCTIVE BODY CONTACT

FIELD

This application relates to medical devices, more particularly implantable leads and extensions for delivering electrical signals.

BACKGROUND

The medical device industry produces a wide variety of electronic and mechanical devices for treating medical conditions. Commonly used neuromodulators include an implantable signal generator and at least one lead. Such devices are commonly utilized to treat numerous conditions in various portions of the body.

Magnetic resonance imaging (MRI) is commonly used to diagnose many disorders and conditions in many parts of the body. MRI scans utilize strong magnetic fields to produce diagnostic images. Concerns have arisen regarding possible undesirable interactions between the environment created during an MRI scan and implantable medical devices. Implantable medical devices and components thereof fabricated in order to alleviate concerns in an MRI environment would be advantageous.

BRIEF SUMMARY

An implantable medical device comprising: a body comprising a proximal end portion configured to be at least partially received by an apparatus, and a distal end portion; a stimulating electrical element at the distal end portion of the body; a stimulating contact at the proximal end portion of the body, wherein the stimulating contact is positioned such that, when received by the apparatus, at least a portion of the apparatus is capable of electrically coupling to the stimulating contact; a stimulating conductor that electrically couples the stimulating electrical element to the stimulating contact; a conductive body, wherein the conductive body is not utilized for application of stimulation; a conductive body contact, wherein the conductive body is electrically connected to the conductive body contact.

A system comprising: the implantable medical device described herein, and the apparatus by which the device described herein is configured to be received.

An implantable medical system comprising: an extension comprising: a) an extension body comprising a proximal end portion configured to be at least partially received by an apparatus, and a distal end portion; a stimulating electrical element at the distal end portion of the extension body; a stimulating contact at the proximal end portion of the extension body, wherein the stimulating contact is positioned such that, when received by the apparatus, at least a portion of the apparatus is capable of electrically coupling to the stimulating contact; a stimulating conductor that electrically couples the stimulating electrical element to the stimulating contact; a conductive body, wherein the conductive body is not utilized for application of stimulation; a conductive body contact that is electrically connected to the conductive body; and b) a lead comprising: a lead body having a proximal end portion configured to be at least partially received by the extension, and a distal end portion; an electrode at the distal end portion of the lead body; a stimulating contact at the proximal portion of the lead body, the stimulating contact being electrically coupled to the electrode and being positioned such that when received by the extension, at least a portion of the extension is capable of electrically coupling to the stimulating contact; a conductive body, wherein the conductive body contact of the extension and the conductive body of the lead are configured to electrically connect the conductive body of the lead and the conductive body of the extension.

Figure 1:
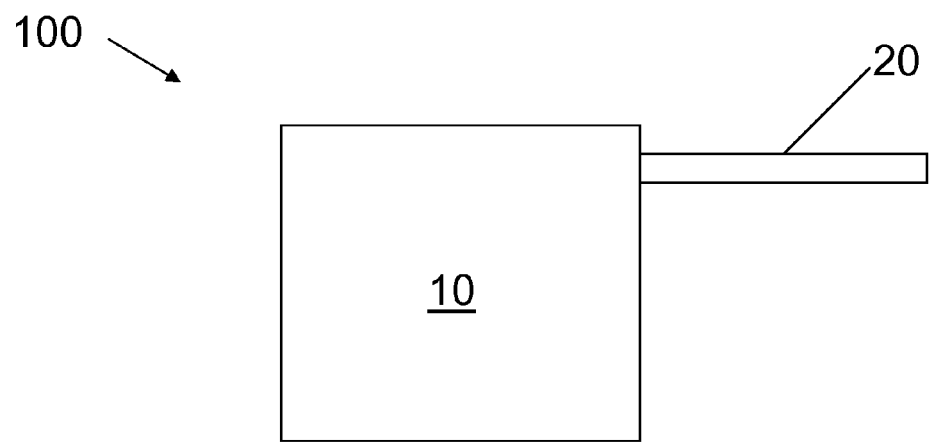
FIG. 1 is a diagrammatic representation of a side view of an implantable electrical signal therapy system.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "proximal" and "distal" refer to position relative to an implantable pulse generator. For example, a proximal portion of a lead or a extension is a portion nearer a signal generator, and a distal portion is a portion further from the signal generator.

As used herein, "signal generator" and "pulse generator" are used interchangeably. It will be understood that a pulse generator may generate an electrical signal or a plurality of electrical signals that are not pulses.

The present disclosure relates to implantable medical devices, such as leads and extensions, comprising conductive bodies integrated into the body of the device. The conductive bodies are configured to provide additional functionality in the device. In an embodiment, the device can be configured so that the conductive body can provide electromagnetic shielding across the device or across an implantable medical system that includes a device as described herein. In an embodiment, the device can be configured so that the conductive body can aid in electromagnetic transmission from the device or from an implantable medical system that includes a device as disclosed herein.

Figure 2:
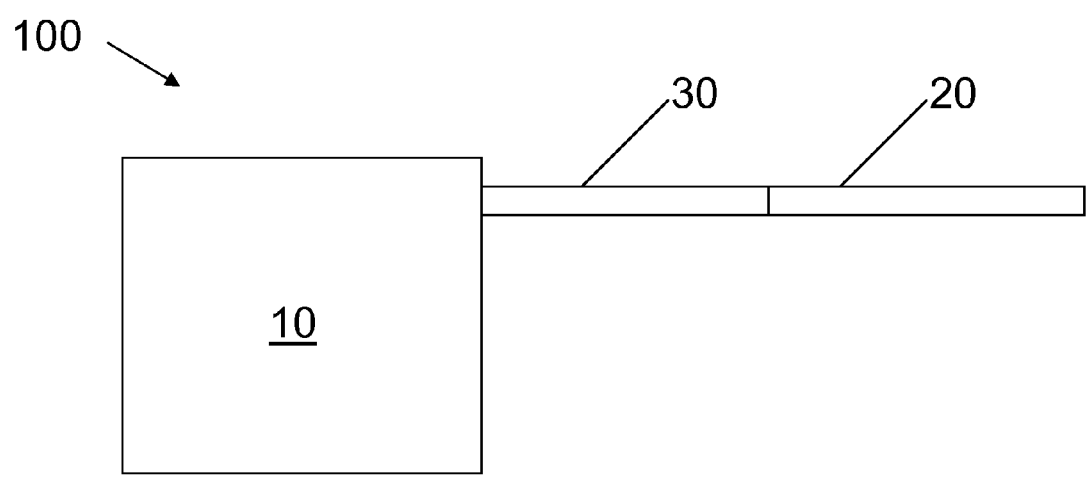
FIG. 2 is a diagrammatic representation of a side view of an implantable electrical signal therapy system.

Referring to FIG. 1, a diagrammatic representation of an implantable electrical signal therapy system 100 is shown. The system 100 comprises an implantable active electrical device 10, and a lead 20 operably coupled to the active electrical device 10. Active electrical device 10 may be any electrical signal generator or receiver useful for delivering therapy to a patient or for patient diagnostics. For example, active electrical device 10 may be a hearing implant; a cochlear implant; a sensing device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. As shown in FIG. 2, system 100 may comprise a extension 30 or other adaptor to couple lead 20 to active electrical device 10. While not shown, it will be understood that more than one lead 20 may be operably coupled to one active electrical device 10 or one extension 30 or that more than one extension 30 may be operably coupled to one active electrical device 10.

Figure 3:
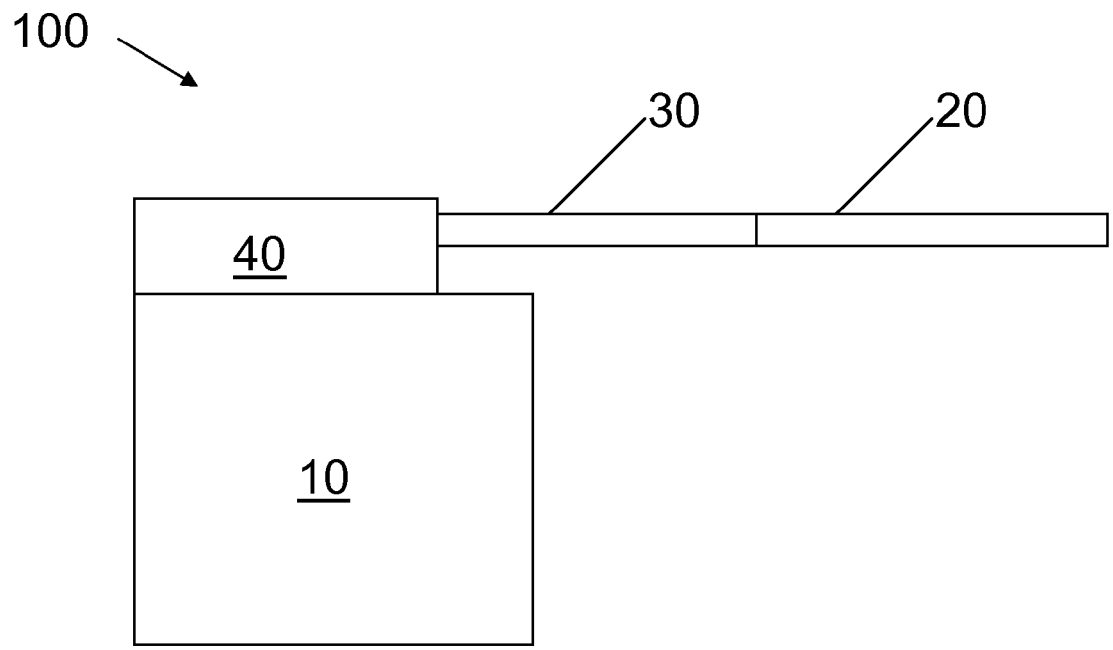
FIG. 3 is a diagrammatic representation of a side view of an implantable electrical signal therapy system.

Referring to FIG. 3, active electrical device 10 may include a connector portion 40 for connecting to lead 20 or extension 30 or other adaptor to couple lead 20 to active electrical device 10. While not shown, it will be understood that lead 20 may be coupled to active electrical device 10 without extension 30 or adaptor.

Figure 4:
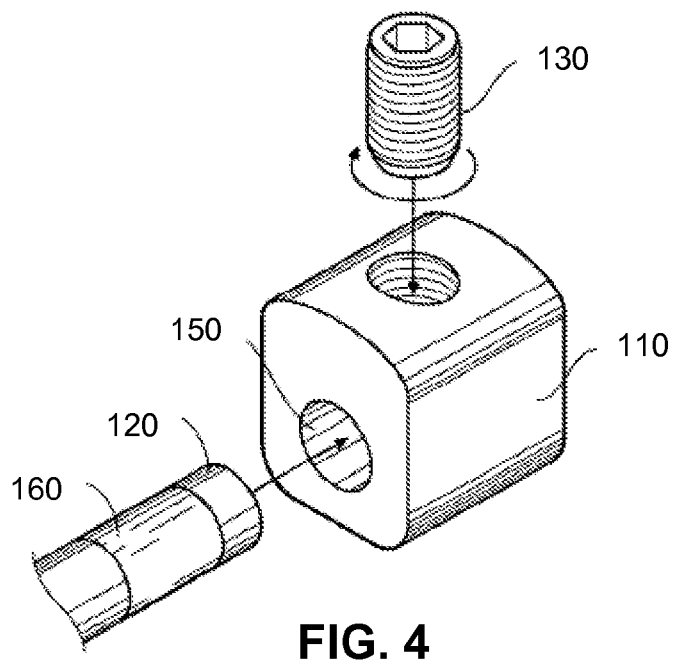
FIG. 4 is an isometric view of a portion of a connector block of a representative implantable electrical signal therapy system.

Referring to FIG. 4, an isometric view of a portion of a body or connector block 110 is shown. Connector block 110 may be included in connector 60 at distal end portion of extension 30 (see, e.g., FIG. 5) or connector portion 40 of active electrical device 10 (see, e.g., FIG. 3). It will also be understood by one of skill in the art that a connector block 110, and/or components thereof could alternatively be included in the proximal portion of lead 20 or the proximal portion of extension 30, for example in the connector 50.

Connector block 110 may be used to secure device 120, which may be a lead, extension, or adaptor to active electrical device, or may be used to secure a lead to an extension or adaptor. Device 120 may be inserted through an axially aligned opening 150 in connector block 110. The connector block 110 shown in FIG. 4 comprises a set screw 130, which may be tightened to apply a compressive force on device 120 to assist in securing device 120 relative to connector block 110, and thus relative to active electrical device 10, extension 30 or adaptor, as the case may be. It will be understood that other suitable methods, including other means for applying compressive force, for securing device 120 relative to connector block 110 may be employed.

Set screw 130 may be used to electrically couple device 120 to connector block 110, and thus to active electrical device, extension or adaptor (as the case may be), by contacting conductive body contact 160 of device 120. Further detail regarding the conductive body contact 160 are presented below. While not shown, it will be appreciated that connector block 110 may comprise a plurality of set screws or other devices to apply compressive force, along is length, which may be configured to align with and contact a plurality of stimulating electrical contacts, as well as conductive body contact 160 of device 120. It will also be understood that an active device, extension, or adaptor, may include a plurality of connector blocks 110.

Compressive force applied to device 120 relative to connector block 110 may be any amount of force to prevent device 120 from pulling out of connector block 110 under implanted conditions. In various embodiments, connector block 110 comprises collapsed springs, such as Balseal rings (not shown), or other elastomeric material (not shown) to provide compressive force, typically at conductive body contact 160. In one embodiment, a conductive body contact comprises collapsed springs, such as Balseal rings, or other elastomeric material in combination with a set screw 130.

Figure 5:
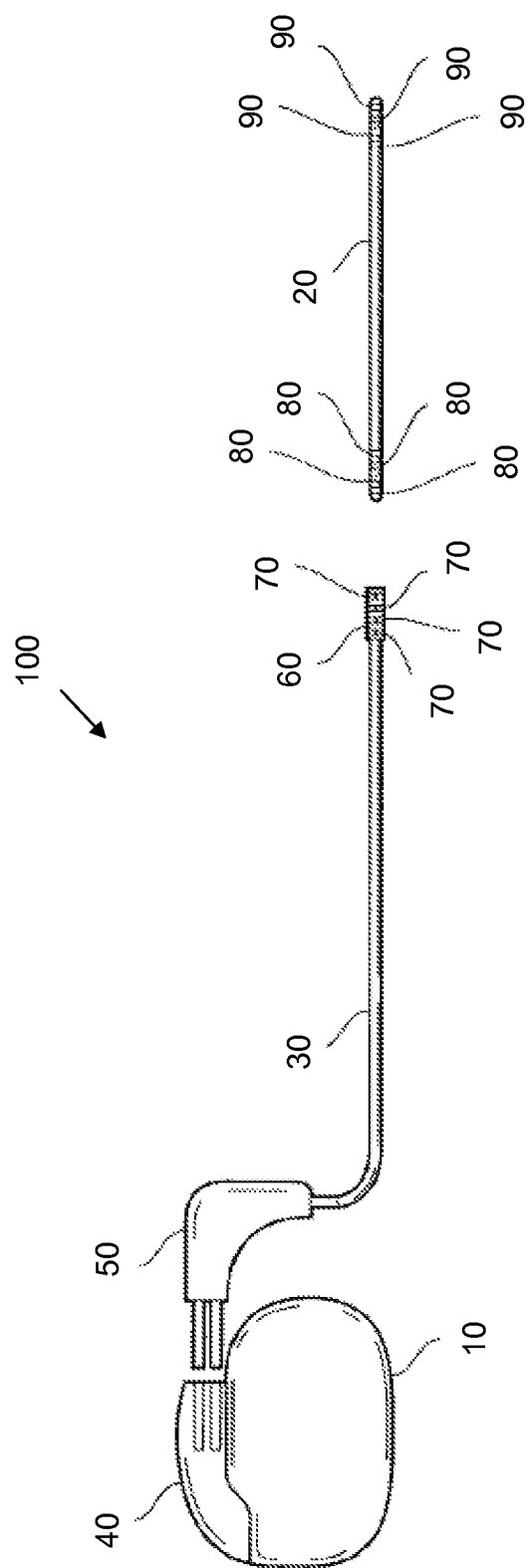
FIG. 5 is an exploded view of a representative implantable electrical signal therapy system.

Referring to FIG. 5, an exploded view of a representative implantable active electrical system 100 is shown. In the system shown in FIG. 5, implantable active electrical device 10 comprises a connector block 40 configured to receive connector 50 at a proximal end of extension 30. The distal end of extension 30 comprises a connector 60 configured to receive proximal end of lead 20. Connector 60 comprises internal stimulating contacts 70 configured to electrically couple extension 30 to lead 20 via stimulating contacts 80 disposed on the proximal end portion of lead 20. Generally, the connector 60 on the distal end of extension 30 is configured to be complementary to the proximal end portion of lead 20. An example of such a complementary configuration is a male and female connector. One of skill in the art will understand, having read this specification that the connector 60 on the distal end of extension 30 can be configured to be either the male or the female connector, and the connector on the proximal end portion of lead 20 can be configured to be of the complementary connector type. Electrodes 90 are disposed on distal end portion of lead 20 and are electrically coupled to stimulating contacts 80, typically through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete stimulating contact 80.

Figure 6:
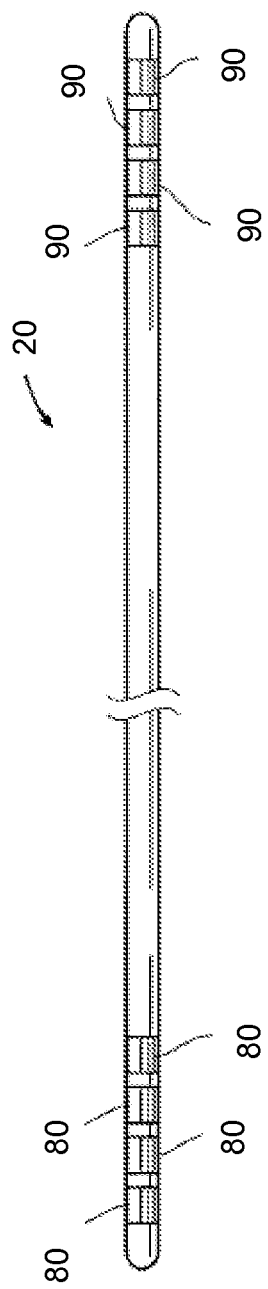
FIG. 6 is a perspective view of a representative lead.
Figure 7:
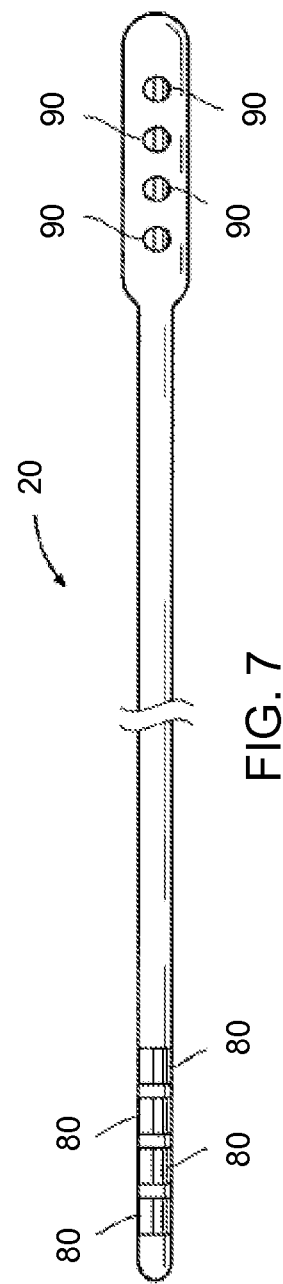
FIG. 7 is a perspective view of a representative lead.

FIGS. 6 and 7 are perspective views of representative leads 20. Leads 20, as shown in FIGS. 6 and 7, contain four exposed stimulating contacts 80 and four electrodes 90. The lead 20 shown in FIG. 7 is a paddle-type lead. However, it will be understood that any lead configuration may be employed in accordance with the teachings provided herein.

Figure 8:
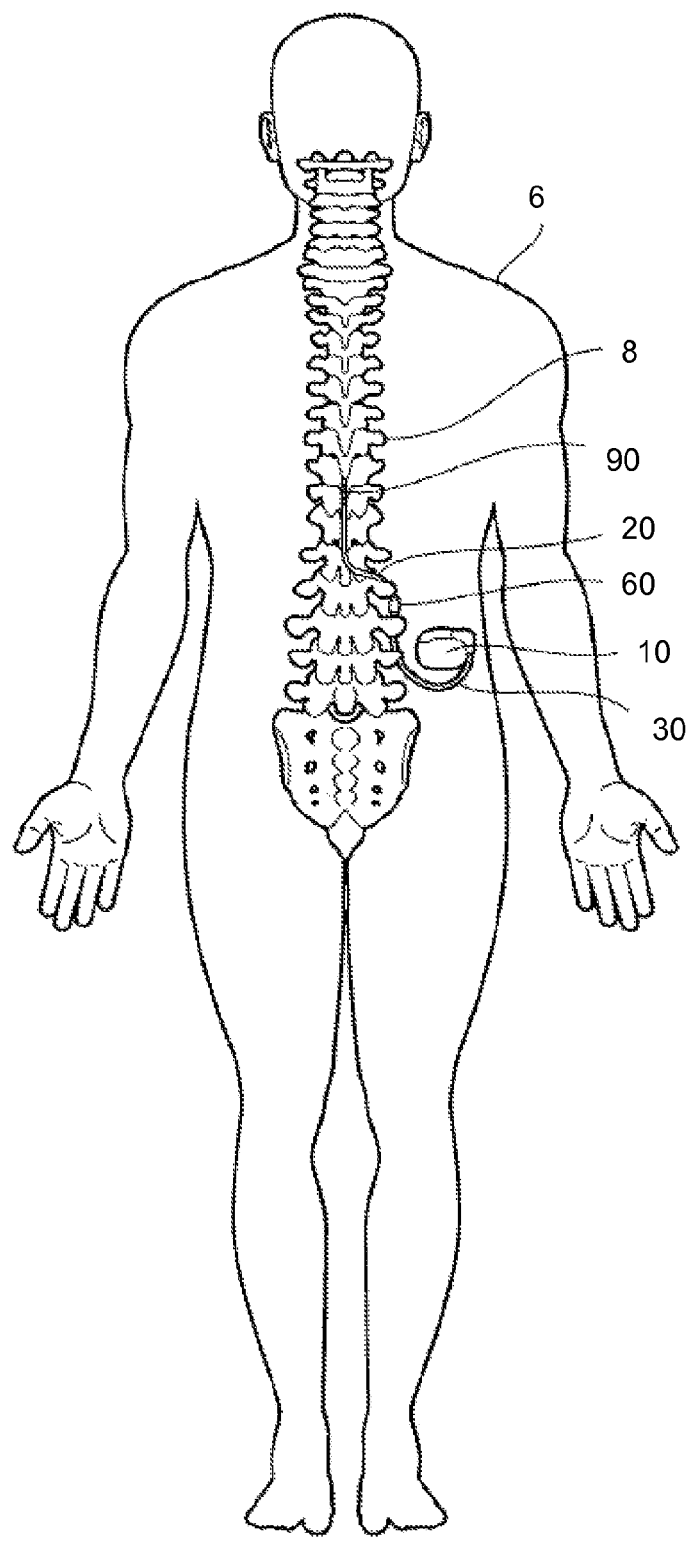
FIG. 8 is a diagrammatic representation of a representative spinal cord stimulation (SCS) system implanted in a patient.

By way of example and referring to FIG. 8, a spinal cord stimulation (SCS) system, is shown implanted in a patient 6. For SCS, an implantable pulse generator (IPG) 10 is typically placed in the abdominal region of patient 6 and lead 20 is placed at a desired location along spinal cord 8. Such a system, or any system including an IPG 10 as described herein, may also include a programmer (not shown), such as a physician programmer or a patient programmer IPG 10 is capable of generating electrical signals that may be applied to tissue of patient 6 via electrodes 90 for therapeutic purposes. IPG 10 contains a power source and electronics for sending electrical signals to the spinal cord 8 via electrodes 90 to provide a desired therapeutic effect. It will be appreciated that other systems employing active electrical devices and therapeutic uses thereof are contemplated.

Figure 9:
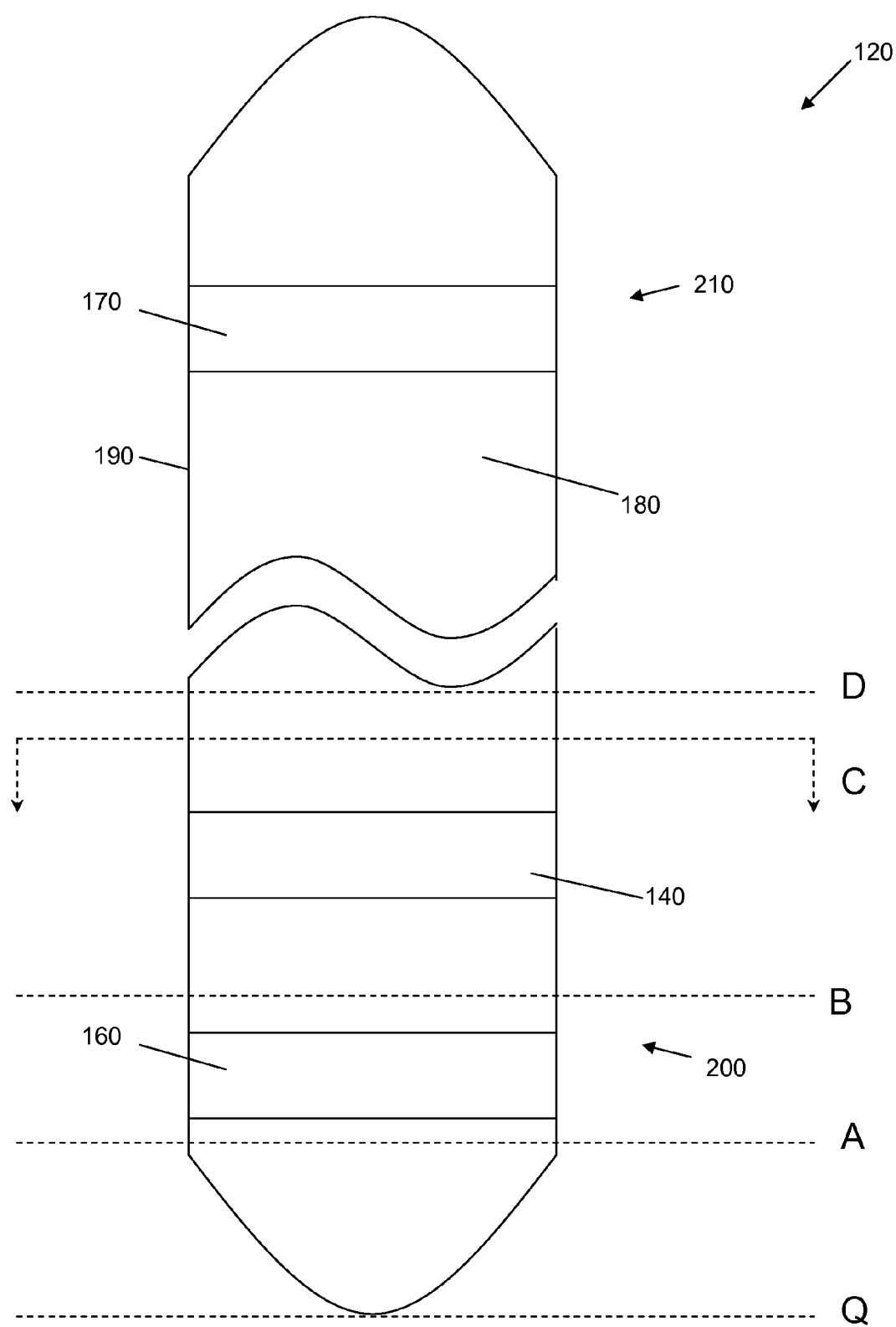
FIG. 9 is a diagrammatic representation of a top view of a representative lead.

Referring to FIG. 9, a diagrammatic representation of a perspective view of a device 120 is shown. Device 120 comprises a body 180, which comprises an external surface 190, a proximal end portion 200 configured to be at least partially received by an apparatus, and a distal end portion 210. In FIG. 9, the portion of the device 120 to be at least partially received by the apparatus is shown as the portion of device 120 between lines D and Q. However, it will be understood that the portion of device 120 to be received by the apparatus may vary depending on the interaction between device 120 and apparatus. Device 120 may be a lead, extension, or adaptor configured to couple an active medical device to a lead or extension. The apparatus may be an active medical device, extension or adaptor. Device 120 includes a stimulating contact 140 and a stimulating electrical element 170 electrically coupled to the stimulating contact 140. Stimulating electrical element 170 may be an electrode, e.g. if device 120 is a lead, or may be a stimulating contact, e.g. if device 120 is an extension or adaptor. A stimulating contact as used herein refers to an electrical connection for a stimulating circuit. While not shown, it will be appreciated that device 120 may comprise a plurality of stimulating contacts 140 and stimulating electrical elements 170. The device 120 also includes a conductive body contact 160. Conductive body contact 160 is electrically connected to the conductive member (not shown in FIG. 9). Conductive member contact 160 is not electrically connected to any portion of the device that is directly involved with providing electrical signals for therapeutic stimulation. Although it is pictured in FIG. 9 that the conductive body contact 160 is positioned proximal the stimulating contact 140, one of skill in the art, having read this specification, will understand that the configuration could be reversed.

Devices as described herein may be made according to any known or future developed process. For example, the body material of devices may be injection molded or extruded. In some situations it may be desirable to reflow body material from thermoplastic polymers. Body material is typically made of polymeric material, such as polyurethane, polycarbonate, or silicone or combinations thereof. Stimulating electrodes may be formed of electrically conductive biocompatible materials, such as platinum or platinum iridium. Stimulating contacts, conductive body contacts, and stimulating conductors may be formed of electrically conductive biocompatible materials, such as platinum, platinum iridium, titanium, tantalum, nickel-cobalt-chromium-molybdenum alloys, or the like. Stimulating conductors may comprise braided strand wire.

A device as disclosed herein also includes a conductive body 220. As exemplified in FIG. 10, the conductive body 220 can be integrated into the body 180 of the device 120. Conductive body 220 can also be located on the outer surface 190 of the device 120. One of skill in the art would know, given the desired additional functionality that the conductive body 220 is to provide, desirable locations and configurations for the conductive body 220.

Conductive body 220 generally provides additional functionality to the device 120. In an embodiment, the conductive body 220 can function to affect the way in which other portions of the device 120 are effected by or interact with electromagnetic radiation. In an embodiment, the conductive body 220 can function to provide electromagnetic shielding for the portions of the device 120 that are effected during an MRI scan. In an embodiment, the conductive body 220 can assist in the transmission of electromagnetic radiation, i.e act as an antenna.

In an embodiment, the conductive body 220 can function to shield portions of the device 120 from the electromagnetic fields produced during an MRI scan, thus reducing the amount of energy reaching portions of the device 120 and therefore decreasing the extent to which portions of the device 120 are heated. This shielding of portions of the device 120 may be accomplished through use of a number of methods and conductive materials. Examples of materials that can be used in the conductive body 220 include, but are not limited to, titanium, stainless steel, and platinum. These metals may be used to form sheets, braids, wires, coils (of a constant or variable pitch), foils, or powders. Additional suitable materials include, but are not limited to, gold plated microspheres, solid particles of conductive polymers, carbon powder, carbon fibers, and intrinsically conductive polymers.

These exemplary shielding materials and formats may be incorporated into the device in a number of ways. Materials and configurations for conductive bodies that will function as electromagnetic shields and methods of making them are known to those of skill in the art. Possible methodologies include shielding the device by imbedding, depositing, implanting, bombarding, coextruding, or ionic plasma deposition. Shielding material may be deposited along with vapor deposited material such as paralene using vapor deposition process. A shielding material may be electrochemically deposited onto the outer surface 190 of the device 120 to shield the device, or a bio-compatible organic coating may be bound to the surface of the device 120 which is infused with shielding material or to which shielding material may be bound. Particular examples of such include, but are not limited to those found in commonly assigned U.S. Patent Publication No. 2005/0222658, titled "LEAD ELECTRODE FOR USE IN AN MRI-SAFE IMPLANTABLE MEDICAL DEVICE".

In an embodiment, the conductive body 220 is configured to have good RF electromagnetic contact with the surrounding body tissue when implanted. In this manner, energy created in the conductive body 220 during an MRI scan can be safely dissipated in the surrounding tissue. Additionally, if the conductive body is in direct contact with the patient's body, the conductive body does not retransmit energy to the device itself. In one embodiment, the conductive body may be configured to be in direct contact with the body tissue when implanted. Such a configuration can more readily assure that energy created in the conductive body is safely dissipated. This may be accomplished by adhering the conductive body to the exterior surface of the device. In another embodiment, the conductive body can be configured to merely reside near the exterior surface of the device so as to easily transmit absorbed RF energy to the body tissue.

In an embodiment where the conductive body 220 functions as an electromagnetic shield, the conductive body contact 160 can function to ground the conductive body, electrically connect one conductive body to another, or both.

Grounding the conductive body 220 can allow energy in the conductive body that is created by the MRI environment to be safely dissipated. Connecting the conductive body 220 in the device 120 to another conductive body in the apparatus (for example a conductive body in a lead) can function to extend the electromagnetic shielding effect across the entirety of the two articles.

The conductive body 220 can also add functionality to the device 120 by enhancing the transmission of electromagnetic radiation. Such functionality could also be referred to as an antenna. Some implantable medical devices and implantable medical systems utilize wireless communication in order to transmit information to or from the implantable medical device inside a patient to external devices such as programmers, for example. A conductive member 220 that functions as an antenna can include a conductive material. Examples of such conductive materials include, but are not limited to titanium, stainless steel, and the like.

Figure 10:
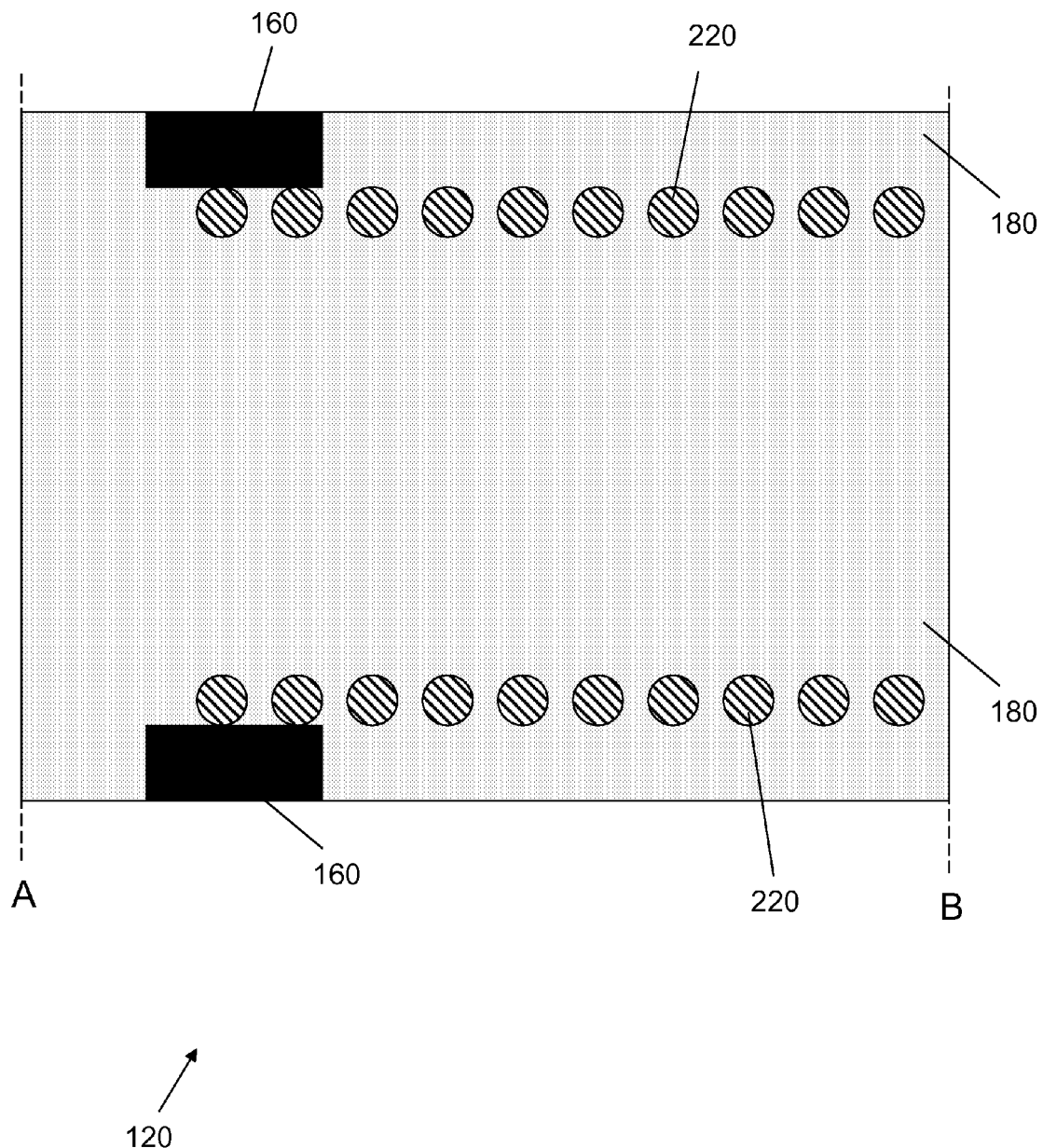
FIG. 10 is a diagrammatic representation of an exemplary longitudinal cross section of an embodiment of the lead shown in FIG. 9 between lines A and B.

FIG. 10 depicts a longitudinal cross section of an exemplary device 120 from line A to line B shown in FIG. 9. For sake of simplicity, FIGS. 10-12 refer to exemplary embodiments of device 120 shown in FIG. 9, which include only one stimulating contact 140 and only one stimulating electrical element 170, and show longitudinal and cross-sectional schematics of embodiments of devices 120. However, it will be understood that device 120 may comprise any number of stimulating contacts 140 and stimulating electrical elements 170.

In the embodiment depicted in FIG. 10, the conductive body 220 is in contact with conductive body contact 160. The conductive body 220 is connected to conductive body contact 160. That is conductive body 220 may be affixed to, fastened to, adhere to, bonded to, captured, or secured to or by, or otherwise attached to conductive body contact 160. In various embodiments, conductive body 220 is connected to conductive body contact 160 such that, when integrated into body 180, conductive body 220 does not separate from conductive body contact 160 when pulled with an average pull force.

Figure 11:
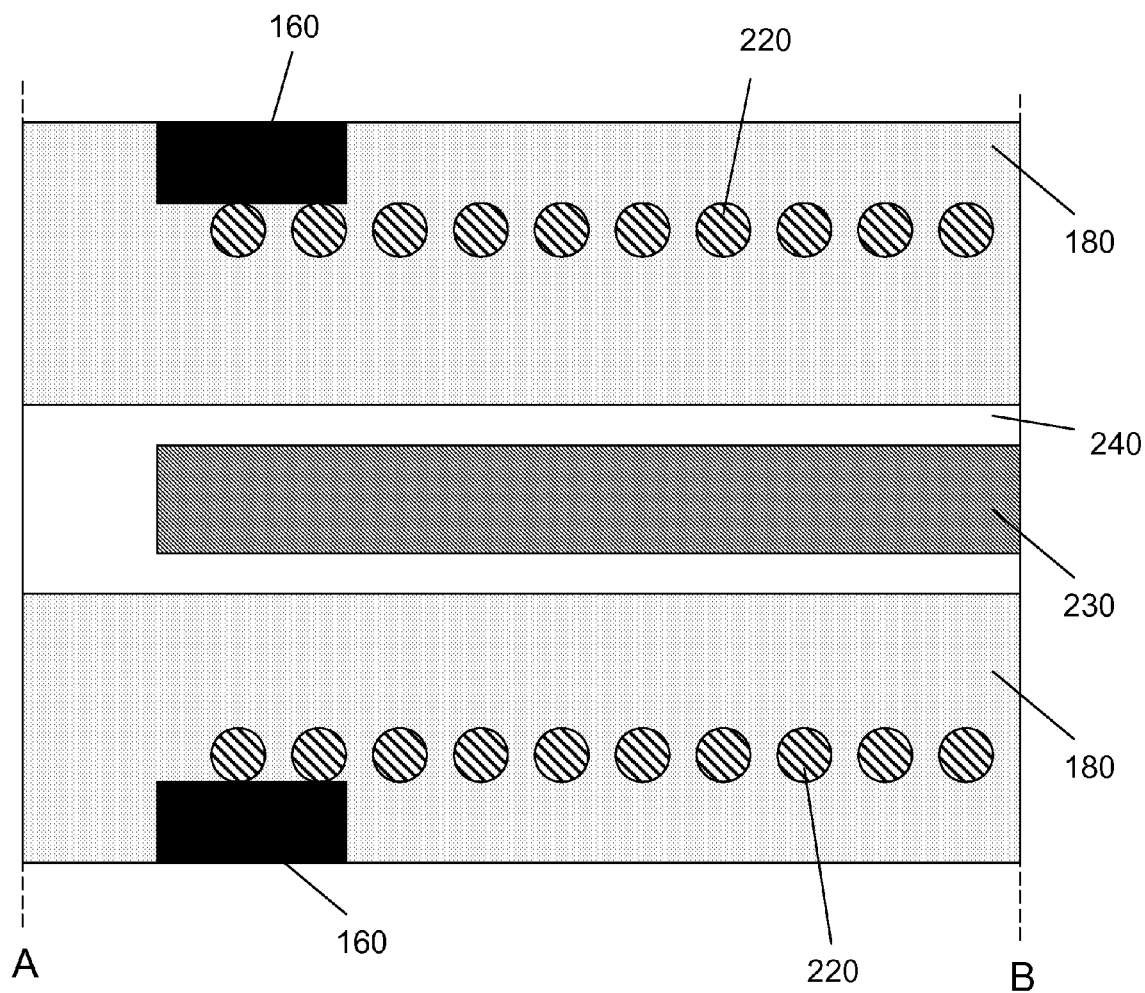
FIG. 11 is a diagrammatic representation of an exemplary longitudinal cross section of an embodiment of the lead shown in FIG. 9 between lines A and B.
Figure 12:
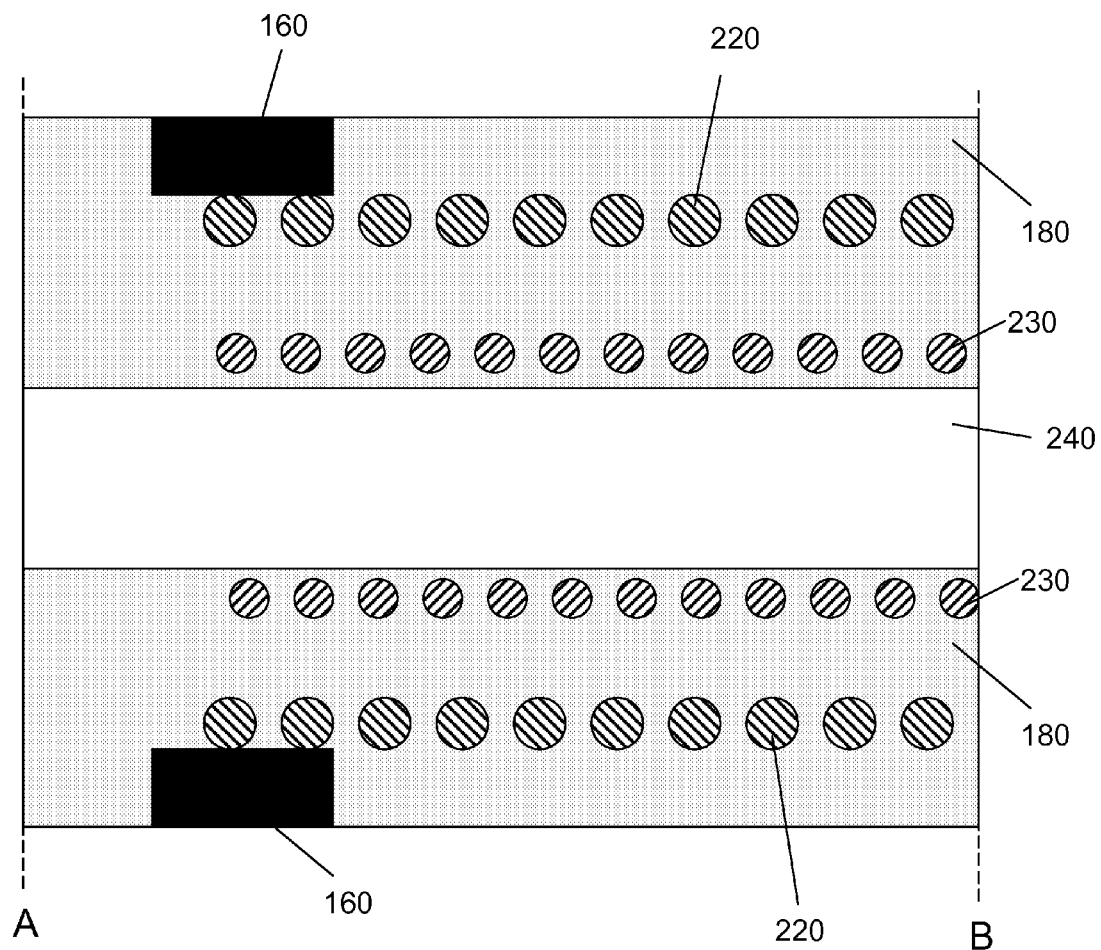
FIG. 12 is a diagrammatic representation of an exemplary longitudinal cross section of an embodiment of the lead shown in FIG. 9 between lines A and B.

As shown in FIG. 11, the device 120 may comprise a lumen 240 through which stimulating conductor 230 may run. Simulating conductor 230 electrically couples stimulating contact 140 to simulating electrical element 170. Stimulating conductor 230 may also be integrated into the material of body 180 of device 120. One example of this is shown in FIG. 12 where the stimulating conductor 230 is wound or otherwise disposed around lumen 240 and/or in material of body 180. Of course, device 120 may have any number of lumens into which conductors, guidewires, stylets, and the like may be placed. Alternatively, device 120 may have no lumen.

A device as described herein, when utilized with an apparatus that also contains a conductive body can provide advantages. In embodiments having a conductive body that functions to shield electromagnetic radiation, a device and an apparatus with a conductive body can extend the shielding function across the device and apparatus because of the electrical connection made by the conductive body contact. For example, when a lead with a conductive body and an extension with a conductive body are connected via a conductive body contact, the electromagnetic shielding extends from the distal reach of the shield on the lead to the proximal reach of the shield on the extension. In embodiments having a conductive body that functions as an antenna, a device and an apparatus with a conductive body can extend the antenna function across the device and apparatus because of the electrical connection made by the conductive body contact. For example, when a lead with a conductive body and an extension with a conductive body are connected via a conductive body contact, the effective length of the antenna is extended from the distal reach of the conductive body on the lead to the proximal reach of the conductive body on the extension.

In an embodiment, another conductive body contact can be included in the apparatus to connect the conductive body in the apparatus to another apparatus. The second (or additional) apparatus can also optionally include a conductive body. In such an embodiment, the conductive body contact in the second apparatus can function to electrically connect the conductive body from the device, through the first apparatus, and through to the second apparatus. In an embodiment where the second apparatus is an implantable medical device such as an implantable signal generator for example, the connection of the conductive body all the way from the lead can function to extend the electromagnetic shield function of the conductive body or provide the antenna function to a device (i.e. the second apparatus) that could benefit from the antenna function. In an embodiment where the conductive body functions as an electromagnetic shield, the connection to the second apparatus can serve to verify that the entire system is shielded from electromagnetic radiation.

The conductive body contact can also function to diminish mechanical stress on the simulation contacts. By mechanically connecting the device and the apparatus via the conductive body contact, axial forces that could be created can be transferred to the conductive body instead of the stimulating connections. Further details regarding this advantage can be found in commonly assigned U.S. patent application Ser. No. 11/627,532, filed on Jan. 26, 2007, entitled "LEAD HAVING REINFORCING MEMBER", the disclosure of which is incorporated herein by reference.

An implantable medical system such as that described herein can also offer another advantage over similar systems that do not utilize a conductive body contact as described herein. When commonly utilized implantable signal generator systems, such as for example those that are commercially available from Medtronic, Inc., are implanted into a patient, the implantation generally includes the connection of a lead to an extension, and the connection of the extension to an implanted signal generator. Both of those connections can utilize at least one set screw, which is accessible from a non-insulated region, i.e. on the surface of the system. This set screw generally forms part of an electrical circuit which is directly involved with the stimulation. Because this set screw is electrically connected to a stimulating circuit, it becomes necessary to place a non-conductive boot around the connection. Generally, this is a polymeric boot that requires additional time during implantation to put in place and suture in place. The device as disclosed herein could eliminate that extra step because the set screw which would make the connection mechanically stable, the set screw in the conductive body contact, is not electrically connected to a stimulating circuit.

Thus, embodiments of a LEAD OR LEAD EXTENSION HAVING A CONDUCTIVE BODY AND CONDUCTIVE BODY CONTACT are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. An implantable medical device comprising:
   a body comprising
      (i) a proximal end portion, and
      (ii) a distal end portion;
   a stimulating electrical element at the distal end portion of the body;
   a stimulating contact at the proximal end portion of the body;
   a stimulating conductor that electrically couples the stimulating electrical element to the stimulating contact;

a conductive body that is integrated into and surrounded by the body, wherein the conductive body is not utilized for application of stimulation and wherein the conductive body has a same depth within the body over the length of the body;

a conductive body contact that is integrated into the body and surrounds and physically contacts the conductive body at the same depth such that the conductive body is electrically connected to the conductive body contact.

2. The implantable medical device of claim 1, wherein the conductive body shields at least a portion of the device from electromagnetic radiation.

3. The implantable medical device of claim 2, wherein the conductive body comprises titanium.

4. The implantable medical device of claim 2, wherein the conductive body contact is configured to extend the shielding effect of the conductive body.

5. The implantable medical device of claim 1, wherein the stimulation electrical element is an electrical contact.

6. The implantable medical device of claim 5, wherein the device is an extension.

7. The implantable medical device of claim 1, wherein the stimulation electrical element is an electrode.

8. The implantable medical device of claim 7, wherein the device is a lead.

9. The implantable medical device of claim 1, wherein the device is an adapter configured to couple a lead or an extension to an implantable signal generator.

10. A system comprising:
an apparatus; and
an implantable medical device comprising:
  a body comprising
    (i) a proximal end portion at least partially coupled to the apparatus, and
    (ii) a distal end portion;
  a stimulating electrical element at the distal end portion of the body;
  a stimulating contact at the proximal end portion of the body, wherein the stimulating contact is positioned such that at least a portion of the apparatus is electrically coupled to the stimulating contact;
  a stimulating conductor that electrically couples the stimulating electrical element to the stimulating contact;
  a conductive body that is integrated into and surrounded by the body, wherein the conductive body is not utilized for application of stimulation and wherein the conductive body is at a same depth within the body over the length of the body;
  a conductive body contact that is integrated into the body and surrounds and physically contacts the conductive body at the same depth;
  wherein the conductive body is electrically connected to the conductive body contact.

11. The system of claim 10, wherein the implantable medical device is a lead and the apparatus is an extension.

12. The system of claim 11, wherein the extension comprises a conductive body that is not utilized for application of stimulation.

13. The system of claim 12, wherein conductive body contact is configured to electrically connect the conductive body of the extension to the conductive body of the lead.

14. The system of claim 10, further comprising a set screw block of the apparatus that receives the proximal end of the device and a set screw that when tightened within the set screw block releasably mechanically attaches the device and the apparatus.

15. An implantable medical system comprising:
an extension comprising:
  an extension body comprising a proximal end portion and a distal end portion;
  a stimulating electrical element at the distal end portion of the extension body;
  a stimulating contact at the proximal end portion of the extension body;
  a stimulating conductor that electrically couples the stimulating electrical element to the stimulating contact;
  a conductive body that is integrated into and surrounded by the extension body, wherein the conductive body is not utilized for application of stimulation;
  a conductive body contact that is integrated into the extension body and is electrically coupled to the conductive body; and
a lead comprising:
  a lead body having a proximal end portion configured to be at least partially received by the extension, and a distal end portion;
  an electrode at the distal end portion of the lead body;
  a stimulating contact at the proximal portion of the lead body, the stimulating contact being electrically coupled to the electrode and being positioned such that when received by the extension, at least a portion of the extension is capable of electrically coupling to the stimulating contact;
  a conductive body that is integrated into and surrounded by the lead body and wherein the conductive body is at a same depth within the lead body over the length of the lead body;
  a conductive body contact that is integrated into the lead body and surrounds and physically contacts the conductive body of the lead at the same depth,
wherein the conductive body contact of the lead body and the conductive body of the extension are configured to electrically connect the conductive body of the lead and the conductive body of the extension.

16. The implantable medical system of claim 15, further comprising a set screw block of the extension that receives the proximal end of the lead and a set screw that when tightened within the set screw block releasably mechanically attaches the lead and the extension.

17. The implantable medical system of claim 15, wherein the conductive body contact of the lead body and the conductive body of the extension are configured to electrically connect the conductive body of the lead and the conductive body of the extension by the conductive body contact of the lead and the conductive body contact of the extension being in contact.

18. An implantable medical system comprising:
an extension comprising:
  an extension body comprising a proximal end portion and a distal end portion;
  a stimulating electrical element at the distal end portion of the extension body;
  a stimulating contact at the proximal end portion of the extension body;
  a stimulating conductor that electrically couples the stimulating electrical element to the stimulating contact;
  a conductive body that is integrated into and surrounded by the extension body, wherein the conductive body is not utilized for application of stimulation and wherein the conductive body is at a same depth within the extension body over the length of the extension body;

a conductive body contact that is integrated into the extension body and surrounds and physically contacts the conductive body of the extension at the same depth; and a lead comprising:
   a lead body having a proximal end portion configured to be at least partially received by the extension, and a distal end portion;
   an electrode at the distal end portion of the lead body;
   a stimulating contact at the proximal portion of the lead body, the stimulating contact being electrically coupled to the electrode and being positioned such that when received by the extension, at least a portion of the extension is capable of electrically coupling to the stimulating contact;
   a conductive body that is integrated into and surrounded by the lead body and;
   a conductive body contact that is integrated into the lead body and is electrically coupled to the conductive body of the lead,
   wherein the conductive body contact of the lead body and the conductive body of the extension are configured to electrically connect the conductive body of the lead and the conductive body of the extension.

* * * * *